United States Patent
Nguyen et al.

(10) Patent No.: US 6,853,215 B1
(45) Date of Patent: *Feb. 8, 2005

(54) PROGRAMMABLE I/O ELEMENT CIRCUIT FOR HIGH SPEED LOGIC DEVICES

(75) Inventors: Khai Nguyen, San Jose, CA (US);
Chiakang Sung, Milpitas, CA (US);
Bonnie Wang, Cupertino, CA (US);
Joseph Huang, San Jose, CA (US);
Phillip Pan, Fremont, CA (US); In Whan Kim, San Jose, CA (US); Gopi Rangan, Santa Clara, CA (US); Yan Chong, Stanford, CA (US); Xiaobao Wang, Santa Clara, CA (US); Tzung-Chin Chang, San Jose, CA (US)

(73) Assignee: Altera Corporation, San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/685,355

(22) Filed: Oct. 9, 2003

Related U.S. Application Data

(63) Continuation of application No. 10/017,666, filed on Dec. 14, 2001, now Pat. No. 6,686,769.

(51) Int. Cl.[7] .......................................... H03K 19/173
(52) U.S. Cl. ............................ 326/46; 326/40; 326/41
(58) Field of Search ............................. 326/38, 39, 40, 326/41, 46

(56) References Cited

U.S. PATENT DOCUMENTS

| 5,581,199 | A | * | 12/1996 | Pierce et al. ................... 326/41 |
| 5,944,813 | A | * | 8/1999 | Trimberger ................... 712/36 |
| 5,960,191 | A | * | 9/1999 | Sample et al. ................ 703/28 |
| 6,020,760 | A | * | 2/2000 | Sample et al. ................ 326/41 |
| 6,300,792 | B1 | * | 10/2001 | Pedersen ...................... 326/38 |
| 6,407,576 | B1 | * | 6/2002 | Ngai et al. ..................... 326/41 |

* cited by examiner

Primary Examiner—Daniel Chang
(74) Attorney, Agent, or Firm—Morgan, Lewis & Bockius LLP

(57) ABSTRACT

A programmable I/O element for an I/O terminal of a logic array is suitable for operating according to high speed 110 modes such as double data rate and zero bus turnaround. The I/O element may include an input block with two registers for registering input signals from the terminal upon alternate clock edges. In addition or alternatively, it may include an output block with two registers that separately register output signals from the array on the same clock edge and a multiplexer that alternately outputs those signals. For bidirectional terminals, the multiplexer output is connectable to the I/O terminal via an output buffer, and an output enable block provides an enable signal to a gating input of the output buffer. Programmable delays may be included in the input, output, and output enable paths, in particular to provide a slower turn-on time than turn-off time for the output buffer.

20 Claims, 7 Drawing Sheets

PROGRAMMABLE I/O ELEMENT CIRCUIT FOR HIGH SPEED LOGIC DEVICES

This application is a continuation of application Ser. No. 10/017,666 filed on Dec. 14, 2001 now U.S. Pat. No. 6,686,769.

FIELD OF INVENTION

The present invention relates to the field of digital circuitry and programmable logic devices. More particularly, it relates to an input/output element circuit in a logic device where the input/output element circuit is suitable for interfacing with circuits or devices that use high speed input/output standards, such as memory using the double data rate and zero bus turnaround input/output standards.

BACKGROUND OF THE INVENTION

Programmable logic devices (PLDs) are integrated circuit devices containing a number of logic elements that can be selectively programmed to implement a wide variety of logic circuit designs. PLDs are commonly used in digital electronic systems together with other devices such as processors, bus drivers, and memory devices. For example, a field programmable gate array (FPGA) is a PLD that contains an array of logic blocks that represent the individual elements of the logic circuit design being implemented. Each logic block is programmably configured and the blocks are programmably interconnected to implement a user's desired logic functions and circuit design. Similarly, a complex PLD (CPLD) has a limited number of relatively large, user-programmable logic blocks—each of which is similar to a small PLD—that communicate with each other across an interconnect matrix.

In a PLD, input/output (I/O) terminals are used to provide data, control, address and clock signals to and from the configured logic blocks in the device. For example, memory controller logic blocks in FPGAs and CPLDs commonly read to and write from memory such as synchronous dynamic random access memory (SDRAM) or static random access memory (SRAM). The memory may be on the same integrated circuit device as the PLD or on a separate device. As used herein, an "I/O terminal" may refer to a terminal that is used as a unidirectional input terminal, exclusively as a unidirectional output terminal, or as a bidirectional terminal that can be configured to act either as an input or an output terminal at any one time. Since the size of a PLD circuit design depends on the number of logic blocks and the number of I/O terminals available, the use of bidirectional I/O terminals is often desirable to permit a given number of logic blocks to be implemented in smaller-sized device. Typically, the I/O terminals are physically implemented in an integrated circuit device as pins, pads, balls or some other type of terminal structure.

An I/O element circuit is often needed to provide an interface between an I/O terminal of a PLD logic array and an external device (or circuit) such as memory. The requirements of an I/O element circuit depend on the type of I/O terminal (i.e., input, output, or bidirectional) and on the I/O standard being used to communicate. Generally, a separate I/O element circuit is associated with each I/O terminal of the PLD. For bidirectional I/O terminals capable of being used for both reads and writes, the I/O element circuit typically provides an output enable (OE) signal that acts to selectively enable/disable write operations via the terminal. I/O element circuits, also referred to as I/O cells, can be programmably implemented as functional logic blocks, similar to the blocks in a PLD logic array.

Two I/O standards in particular, double data rate (DDR) and zero bus turnaround (ZBT), are frequently used in high speed data transfer applications. In the DDR I/O standard, data is clocked on both the rising and falling edge of a clock signal, effectively doubling the data rate of DDR SRAMs and SDRAMs. With the ZBT standard, synchronous fast SRAM devices are designed to provide 100% bus utilization by eliminating all idle clock cycles when turning the data bus around from a write operation to a read operation (or vice versa). This enables considerably faster operation in systems that require frequent and random read and write access, such as in networking and telecommunications applications.

In view of the above, there is a need for an I/O element circuit capable of allowing a logic device's I/O terminal to operate in high speed data modes, especially a DDR I/O mode and a ZBT I/O mode. It would be particularly desirable if such an I/O element circuit were capable of being programmably configured to operate in the different I/O modes.

SUMMARY OF THE INVENTION

The present invention provides a programmable I/O element circuit for an I/O terminal of a logic array that is suitable for allowing the array to interface with, e.g., a memory device using high speed I/O modes such as DDR and ZBT I/O modes. The I/O element circuit includes an input block for unidirectional input I/O terminals, an output block for unidirectional output I/O terminals, and both input and output blocks for bidirectional I/O terminals. In one embodiment, the input block includes two input registers for registering input signals from the terminal at alternate clock edges. The output block may also include two output registers that separately register output signals from the array on the same clock edge and a multiplexer that alternately outputs those registered output signals. For a bidirectional terminal, the multiplexer output is connectable to the I/O terminal via a gated output buffer, and an output enable block provides an enable signal to a gating input of the output buffer. Programmable delays are optionally included in the input, output, and output enable paths. In particular, for ZBT modes, a programmable delay circuit in the output enable path may be used to provide a slower turn-on time than turn-off time for the output buffer, thereby avoiding the possibility of bus contention.

The I/O element circuit advantageously allows any regular I/O terminal in a logic array of a PLD or other logic device to be configured for a double data rate I/O standard using double edge clocking, and without increased clock to-output delays in the I/O element circuit in comparison to single data rate modes. This provides a flexible way of increasing system bandwidth without requiring a higher operating core frequency and helps reduce the board and packaging costs associated with a PLD. In addition, by also accommodating ZBT I/O modes, the programmable I/O element provides increased bandwidth at the same bus frequencies in applications that require a mixture of reads and writes.

Thus, the present invention provides a programmable I/O element circuit for an I/O terminal of a logic array that includes an input block, an output block and an output enable block. The input block includes a first input register having an input for receiving a signal at the I/O terminal and an output for registering the I/O terminal signal upon a first edge in an input clock signal. The output of the first input register is connectable to the logic array, e.g., via a programmable multiplexer. The input block also includes a second input register having an input for receiving the I/O terminal signal and an output for registering the I/O terminal signal upon a second edge in the input clock signal. The output of the second input register can also be coupled to the logic array, e.g., again via a programmable multiplexer. Alternatively, the input block includes an input bistable circuit having an input for receiving the registered I/O terminal signal output by the second input register and an output for latching the registered I/O terminal signal upon the first edge in the input clock signal. In this case, the output of the bistable circuit is connectable to the logic array.

The output block circuit includes a first output register having an input for receiving a first output signal from the logic array and an output for registering the first output signal upon a first edge in an output clock signal. A second output register has an input which, in at least one mode of operation (in particular, a DDR mode), receives a second output signal from the logic array and an output for registering the second output signal upon the first edge in the output clock signal. The output block circuit may also include a multiplexer having a first input connected to the output of the first output register, a second input connected to the output of the second output register, an address input configurable to receive the output clock signal, and an output connectable to the I/O terminal via a gated output buffer. In one embodiment, the input clock signal and output clock signal are provided by different clock sources.

The output enable block circuit receives an enable signal from the logic array and provides an output enable signal to a gating input of the output buffer. The output enable block circuit may include a first output enable register having an input for receiving the enable signal from the logic array and an output for registering a first registered enable signal upon the first edge in the output clock signal. This block can also include a second output enable register having an input for receiving the registered enable signal from the first output enable register and having an output for registering a second registered enable signal upon a second edge in the output clock signal. A logic circuit, e.g., an OR gate, can provide a combined registered enable signal that is connectable as the output enable signal to the gating input of the gated output buffer.

In another embodiment, the present invention provides a programmable I/O element circuit for a bidirectional I/O terminal of a logic array which includes an input register, an output register, and an output enable circuit. The input register has an input for receiving a signal at the I/O terminal and an output for registering the I/O terminal signal upon a first edge in an input clock signal. The output of the first input register is connectable to the logic array. The output register has an input for receiving an output signal from the logic array and an output for registering the output signal upon a first edge in an output clock signal. The registered output signal is connectable to the I/O terminal via a gated output buffer. The output enable circuit receives an enable signal from the logic array and provides an output enable signal to a gating input of the gated output buffer via a programmable delay circuit, wherein the output enable signal provides a slower turn-on time than turn-off time for the gated output buffer. The programmable delay circuit may include a logic gate having first and second inputs and an output. The first logic gate input receives a signal input to the programmable delay circuit, the second logic gate input receives a delayed version of the signal input to the programmable delay circuit, and the output of the logic gate provides the output enable signal.

BRIEF DESCRIPTION OF THE DRAWINGS

The objects and advantages of the present invention will be better understood and more readily apparent when considered in conjunction with the following detailed description and accompanying drawings which illustrate, by way of example, preferred embodiments of the invention and in which.

DETAILED DESCRIPTION OF PREFERRED EMBODIMENTS

Figure 1:
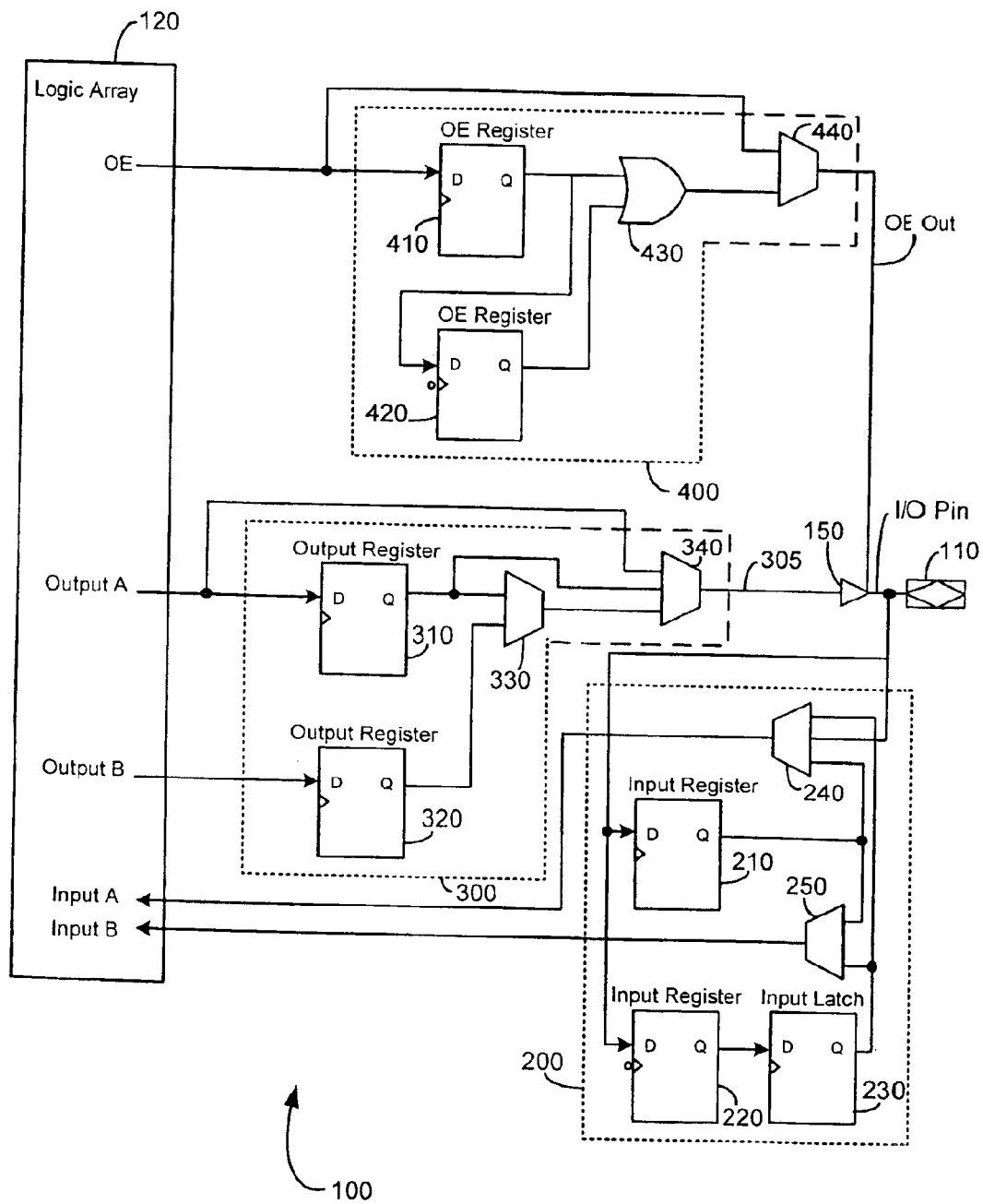
FIG. 1 is a block diagram overview of an I/O element circuit for a bidirectional I/O terminal in accordance with an embodiment of the present invention.

In accordance with an embodiment of the present invention, FIG. 1 is a block diagram overview of an I/O element circuit 100 connected to a bidirectional I/O terminal 110 of a logic array 120. I/O element circuit 100 includes an input block circuit 200, an output block circuit 300, and an output enable block circuit 400. Generally, input block 200 receives an I/O Pin signal present at terminal 110 and provides two programmably selectable signals, Input A and Input B, to logic array 120. Input block 200 includes a first input register 210, a second input register 220, an input latch 230, a programmable selection multiplexer 240 for Input A, and a programmable selection multiplexer 250 for Input B. Output block 300 receives an Output A signal and Output B signal from logic array 120 and provides a programmable signal 305 to I/O terminal 110 via a gated output buffer (i.e., driver) 150. Output block 300 includes a first output register 310, a second output register 320, and two programmable output selection multiplexers 330 and 340. Output enable block 400 receives a signal OE from logic array 120 and provides an OE Out signal that acts as the gating input to output buffer 150. In the illustrated embodiment, buffer 150 passes signal 305 to I/O terminal 110 when the OE Out signal is high, and the output of buffer 150 enters a high impedance state when OE Out is low. Output enable block 400 includes a first OE register 410, a second OE register 420, an OR gate 430, and a programmable multiplexer 440 for selecting OE Out.

The registers in blocks 200, 300, and 400 may be implemented using any suitable bistable circuit capable of holding binary information, and therefore these 1-bit registers may be formed by a flip-flop or, in some instances, also by a latch. Also, as described further below, input latch 230 may also be replaced by another type of bistable circuit, such as a flip-flop. In addition, the programmable multiplexers may generally be any type of device capable of providing a programmable connection or coupling. A more detailed description of structural embodiments for each of blocks 200, 300, and 400 is given below in connection with FIGS. 2, 3, and 4 respectively.

Logic array 120 forms part of a logic device, which may be a PLD such as an FPGA or CPLD memory controller. It will be appreciated that logic array 120 typically includes one or more logic cores (not specifically shown in FIG. 1), each of which is generally divided into a plurality of logic blocks. The Input A, Input B, Output A, Output B, and OE signals may be provided to or from different logic cores in array 120.

Although only one I/O terminal 110 is shown in FIG. 1, logic array 120 generally has a large number of I/O terminals associated with it, and these may be bidirectional, dedicated input, or dedicated output I/O terminals. Each I/O terminal has its own associated I/O element circuit so that I/O signals at that terminal can be suitably interfaced between array 120 and circuits or devices that operate according to various high speed I/O standards, such as the DDR and ZBT I/O standards. For bidirectional I/O terminals 110, the I/O element circuit includes an input block 200, output block 300, and output enable block 400. Alternatively, for a dedicated (unidirectional) input I/O terminal a corresponding I/O element circuit generally need only include an input block 200, and for a dedicated (unidirectional) output I/O terminal a corresponding I/O element circuit need only include an output block 200. Also, the output buffer of each output or bidirectional I/O terminal is preferably controlled by its own output enable block 400.

Figure 2:
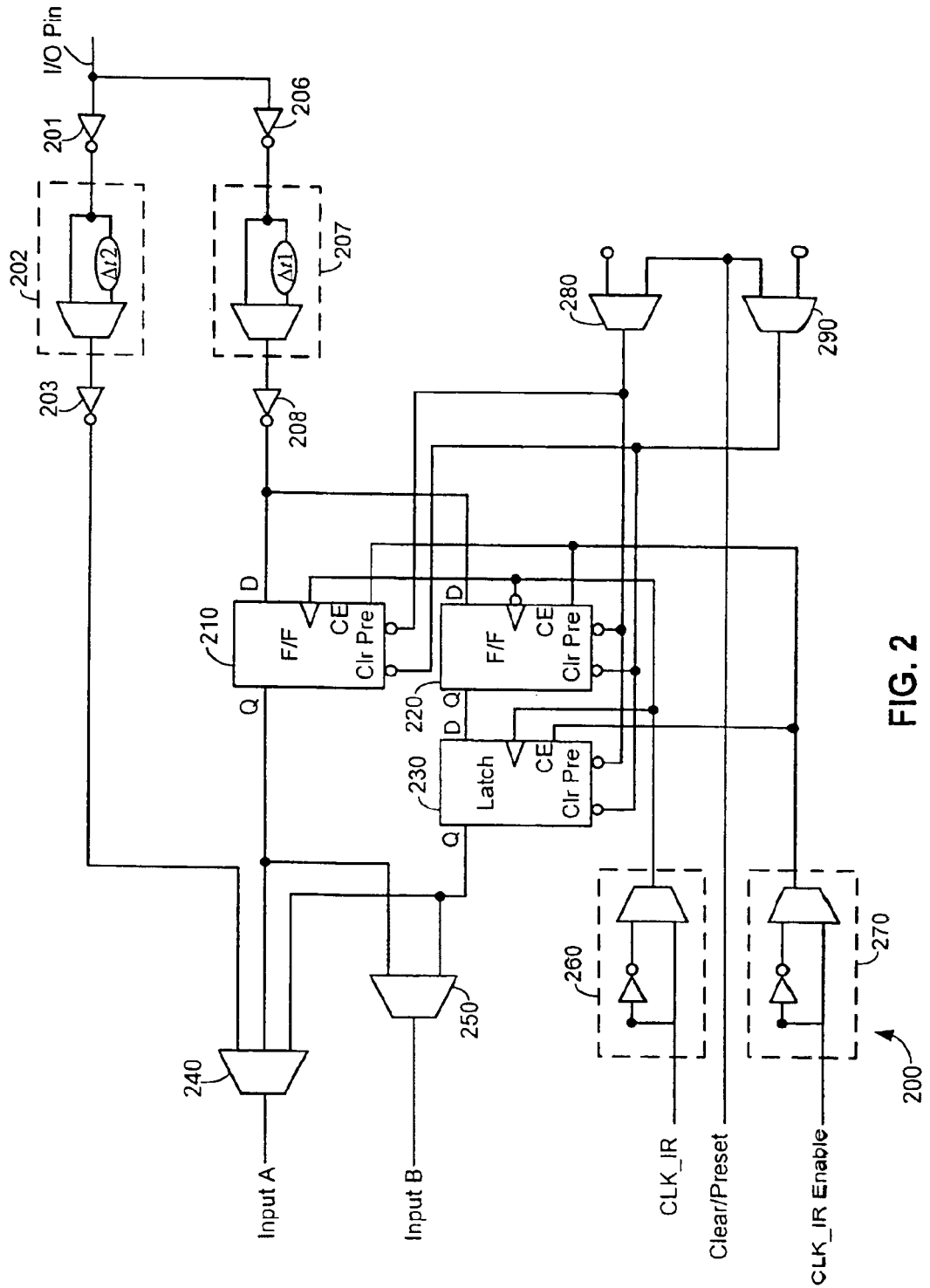
FIG. 2 is a more detailed circuit diagram of the input I/O element block in the circuit of FIG. 1.

FIG. 2 is a more detailed circuit diagram of input block 200 in I/O element circuit 100. As shown, input registers 210 and 220 are implemented as D-type (delay) flip-flops and input latch 230 as a gated D-type latch. The I/O Pin signal present at the I/O terminal is provided through a first inverting buffer 206, a programmable delay (of $\Delta t1$) stage 207, and a second inverting buffer 208 to the inputs of each of registers 210 and 220. The programmable delays may be implemented, for example, using chains of inverters. The output of register 220 is connected to the input of latch 230. For increased flexibility, the output of register 210 and the output of latch 230 are provided as inputs to both programmable multiplexer 240 and programmable multiplexer 250. Multiplexer 240 also receives an "unregistered" version of the I/O pin signal via a first inverting buffer 201, a programmable delay (of $\Delta t2$) stage 202, and a second inverting buffer 203.

As shown in FIG. 2, each of the programmable delay stages 202 and 207 include a programmable multiplexer having delayed and non-delayed versions of the buffered I/O Pin signal as inputs, so that the inclusion of delay in the registered or unregistered input path is a programmable setting. Furthermore the length of the delays $\Delta t1$ or $\Delta t2$ may also be a programmable parameter that can be automatically set using appropriate hardware definition language software. The inclusion of delay in stage 202 and/or 207 may be required or desirable to minimize the hold time for the Input A and Input B signals. The hold time (Th) is the time interval immediately following the mid-point of the active clock edge during which data must be held stable in order to be recognized. The set-up time (Tsu) is the time interval immediately preceding the mid-point of the active clock edge during which data must be held stable to be recognized.

Input register 210 is triggered by the rising edge of an input block clock signal CLK_IR, and input register 220 is triggered by the falling edge of CLK_IR. Each CLK_IR input to registers 210 and 220 is gated by a corresponding CLK_IR enable signal that is provided to the CE input of the registers, as shown. Similarly, level-sensitive latch 230 is gated by a high CLK_IR signal received at its clock/control input, and that clock input is again enabled by the CLK_IR enable signal. Latch 230 is thus enabled when both the CLK_IR signal and CLK_IR enable signal are high. As shown in FIG. 2, both the CLK_IR and the CLK_IR enable signal paths may include programmable inversion stages 260 and 270 respectively, so that the polarity of each of these signals is also a selectable parameter within input block 200. This avoids having to route both phases (i.e., 0° and 180°) of each of the signals to block 200.

A Clear/Preset signal, which may be a global Clear/Preset signal for the entire I/O element circuit 100, drives each of register 210, register 220, and latch 230. As shown, the Clear/Preset signal is routed to the active low preset (Pre) inputs of register 210, register 220, and latch 230 through a programmable multiplexer 280, and the Clear/Preset signal is also routed to the active low clear (Clr) inputs of register 210, register 220, and latch 230 through a programmable multiplexer 290. By programmably setting multiplexers 280 and 290, input block 200 can be configured to power up either low or high in response to a low-level asynchronous Clear/Preset signal.

Figure 3:
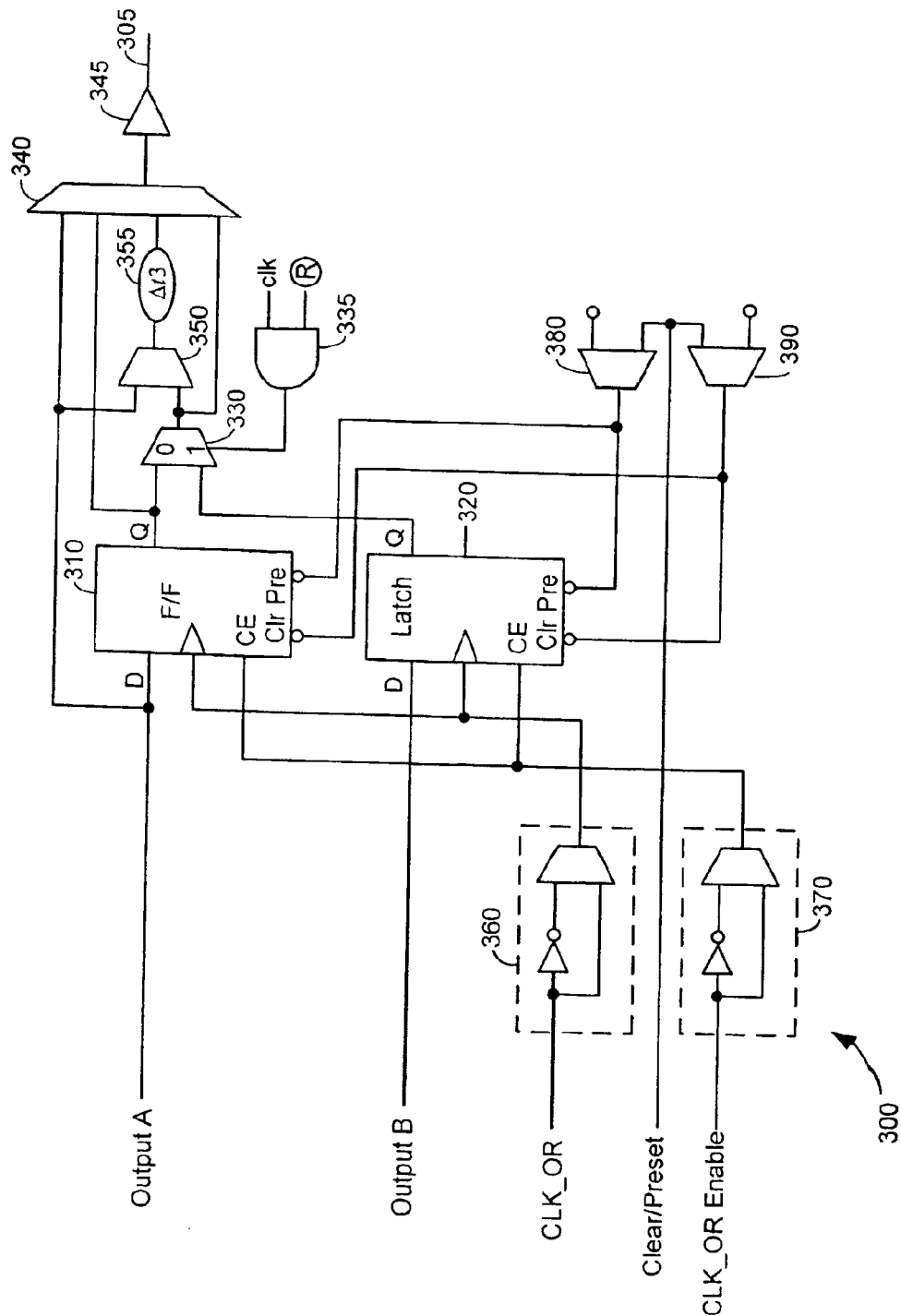
FIG. 3 is a more detailed circuit diagram of the output I/O element block in the circuit of FIG. 1.

Referring now to FIG. 3, a more detailed circuit diagram of output block 300 in I/O element circuit 100 is shown. The first output register 310 may be a D-type flip-flop and receives the Output A signal at its input. The second output register 320 may be a gated D-type latch and receives the Output B signal at its input. The outputs of register 310 and of register 320 are provided as inputs to programmable multiplexer 330 whose address input is the output of an AND gate 335. The inputs to AND gate 335 are a programmable signal R, which may be set either high or low, and a clk signal, which may be from the same source as the CLK_OR signal (see below). As shown, in the illustrated embodiment of FIG. 3, multiplexer 330 is configured to pass the output of register 310 when its programmable address input is 0 and to pass the output of register 320 when its programmable address input is 1. Programmable multiplexer 340 has four inputs including the output of multiplexer 330, the output of register 310, and the unregistered Output A signal. The output of multiplexer 330 and the unregistered Output A signal are also provided as inputs to a programmable multiplexer 350, which provides a delayed (by $\Delta t3$) version of a selected one of those signals to another input of programmable multiplexer 340. The programmable delay $\Delta t3$ via the multiplexer 350 path may be used to improve the clock-to-output time of output stage 300 in some applications.

Referring still to FIG. 3, output register 310 is triggered by the rising edge of an output block clock signal CLK_OR. Although the CLK_IR and CLK_OR signals are of the same frequency and may be derived from the same master clock, they are provided by different clock sources in the illustrated embodiments. This permits separate phase/time delay control of CLK_IR and CLK_OR and thereby facilitates the control of timing parameters such as the set-up time (Tsu), hold time (Th), and clock-to-output time (Tco). As shown, the CLK_OR input to register 310 is gated by a corresponding CLK_OR enable signal provided to the CE input of register 310. Similarly, the level-sensitive latch acting as register 320 is gated by a high CLK_OR signal received at its clock/control input, with that clock input again being enabled by the CLK_OR enable signal. As a result, register 320 is enabled when both the CLK_OR signal and CLK_OR enable signal are high. As in input block 200, to avoid having to route both phases of the CLK_OR and the CLK_OR enable signals to output block 300, each of those signal paths may include a programmable inversion stage, as shown at 360 and 370 respectively.

The Clear/Preset signal—which, as mentioned above, may be a global Clear/Preset signal for I/O element circuit 100—drives register 310 and register 320. The Clear/Preset signal is routed to the active low preset (Pre) inputs of register 310 and register 320 through a programmable multiplexer 380 and to the active low clear (Clr) inputs of register 310 and register 320 through another programmable multiplexer 390. By appropriately programming multiplexers 380 and 390, output block 300 can be configured to power up either low or high in response to a low-level asynchronous Clear/Preset signal.

Figure 4:
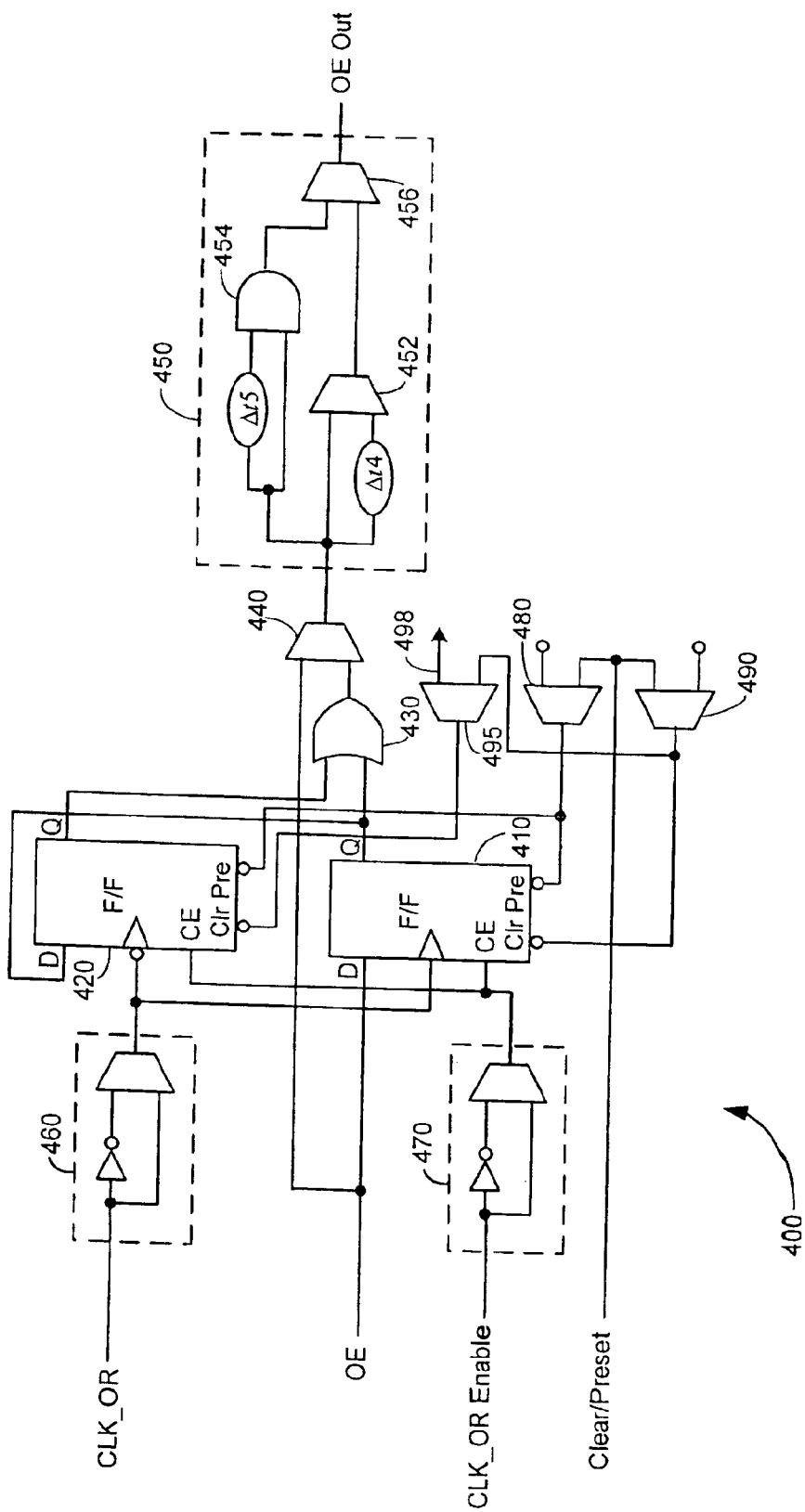
FIG. 4 is a more detailed circuit diagram of the output enable I/O element block in the circuit of FIG. 1.

Referring now to FIG. 4, a more detailed circuit diagram of output enable block 400 in I/O element circuit 100 is shown. As shown, OE registers 410 and 420 may be implemented as D-type flip-flops. The OE signal from logic array 120 is provided to the input of register 410. The output of register 410 is provided as the input to OR gate 430 and as the input to register 420. The output of register 420 is also connected as an input of OR gate 430. The output of OR gate 430 and the unregistered OE signal are provided as inputs to programmable multiplexer 440. It will be appreciated that other logic circuits with the same functionality can be used in place of OR gate 430 to combine the registered outputs of registers 410 and 420. The output of multiplexer 440 is fed to a programmable delay circuit 450 which includes a first programmable multiplexer 452, an AND gate 454, and a second programmable multiplexer 456. Multiplexer 452 receives the output of multiplexer 440 directly at one input and a first delayed (by Δt4) version of the multiplexer 440 output at another input. Similarly, AND gate 454 directly receives the output of multiplexer 440 at a first input, while a second delayed (by Δt5) version of the multiplexer 440 output is provided to the other input of AND gate 454. The outputs of multiplexer 452 and of AND gate 454 are each provided as inputs to multiplexer 456, and the output of multiplexer 456 provides the OE OUT signal from output enable stage 400. Programmable delay circuit 450 thus selectively permits either a non-delayed or a delayed version of the output of multiplexer 440 to be provided as OE Out. Furthermore, as described further below, the upper delay path in circuit 450 that includes AND gate 454 is particularly suitable for ZBT applications where it is desirable to increase the output buffer/driver 150's turn-on time for the appearance of output signals on I/O terminal 110.

Referring still to FIG. 4, OE register 410 is triggered by the rising edge of output block clock signal CLK_OR, while OE register 420 is triggered by the falling edge of CLK_OR. Thus, the clock signal for block 400 may be from the same clock source as that for output block 300. The CLK_OR input to each of registers 410 and 420 is gated by the corresponding CLK_OR enable signal provided to the CE input of each register. Similar to the input and output blocks in I/O element 100, each of the CLK_OR and the CLK_OR enable signal paths can include a programmable inversion stage, as shown at 460 and 470 respectively, to avoid any requirement to route both phases of those signals to output enable block 400.

The global Clear/Preset signal for I/O element circuit 100 is used for both OE registers 410 and 420. The Clear/Preset signal is routed to the active low preset (Pre) inputs of register 410 and latch 420 through a programmable multiplexer 480. That signal is also routed to the active low clear (Clr) input of register 410 through another programmable multiplexer 490. For register 420, however, the output of multiplexer 490 is first fed to the input of yet another programmable multiplexer 495 whose other input 498 is tied low. Thus, whenever multiplexer 495 is configured to pass the low input 498 to the active low clear input of register 420, that register is turned off and the output of OR gate 430 follows the output of register 410. Otherwise, by appropriately programming multiplexers 480, 490, and 495, both registers in output enable block 400 can be configured to power up either low or high in response to a low-level asynchronous Clear/Preset signal.

The I/O element circuit of the present invention is especially suitable for bidirectional I/O terminals of a memory controller PLD that interface and communicate with SRAM devices such as DDR SRAMs, quad data rate (QDR) SRAMs, and ZBT SRAMs as well as DRAM devices such as single data rate (SDR) and DDR DRAMs. However, as indicated above, the I/O element circuit may also be adapted for unidirectional input and unidirectional output I/O terminals. The operation of I/O element circuit 100 when operating under various different I/O standards will now be described.

In a standard SDR I/O mode, only one bit is input to or output from logic array 120 during each clock cycle. This may occur upon either the rising or the falling edge of the clock signal. For example, where I/O element 100 is used for bidirectional SDR operation on the rising clock edge, input register 210, output register 310, and OE register 410 are the only bistable circuits needed in each of blocks 200, 300, and 400 respectively. In this case, input register 220 and input latch 230 may, for instance, be programmably tied to a low signal at their active low clear inputs using suitable programmable circuitry (not shown). Alternatively, the output from input register 220 or latch 230 can be programmably disconnected. Also in this mode, in output block 300, the programmable input R to AND gate 335 is set low, so that the address input to multiplexer 330 is always zero (low). With R low, multiplexer 330 only passes the output of output register 310 and so output register 320 has no effect on output stage 400 operation. In addition, in a bidirectional SDR I/O mode, programmable multiplexer 495 in output enable block 400 can be set to pass its tied low input signal 498, so that OE register 420 is cleared. In some SDR applications, in particular, it may be desirable for the input, output, and output enable signals to pass through I/O element 100 unregistered. As described above, I/O element circuit 100 is flexible enough to accommodate such applications by appropriately configuring programmable multiplexers 240, 340, and 440 in blocks 200, 300, and 400, respectively.

In DDR I/O mode, two bits are clocked during a clock cycle, one during the clock's rising edge and one during the clock's falling edge. The I/O element circuit of the present invention advantageously allows any standard I/O terminal to be interfaced according to the DDR I/O standard. An I/O terminal may be configured for a bidirectional DDR mode, a unidirectional DDR input mode, or for a unidirectional DDR output mode. When separate read and write unidirectional I/O terminals are configured for DDR I/O but are associated with the same address line, four bit throughput per clock cycle is effectively achieved to provide quad data rate (QDR) operation. In this case, the unidirectional read I/O terminal has an I/O element that includes input block 200, and the unidirectional write I/O terminal has an I/O element that includes output block 300.

Figure 5:
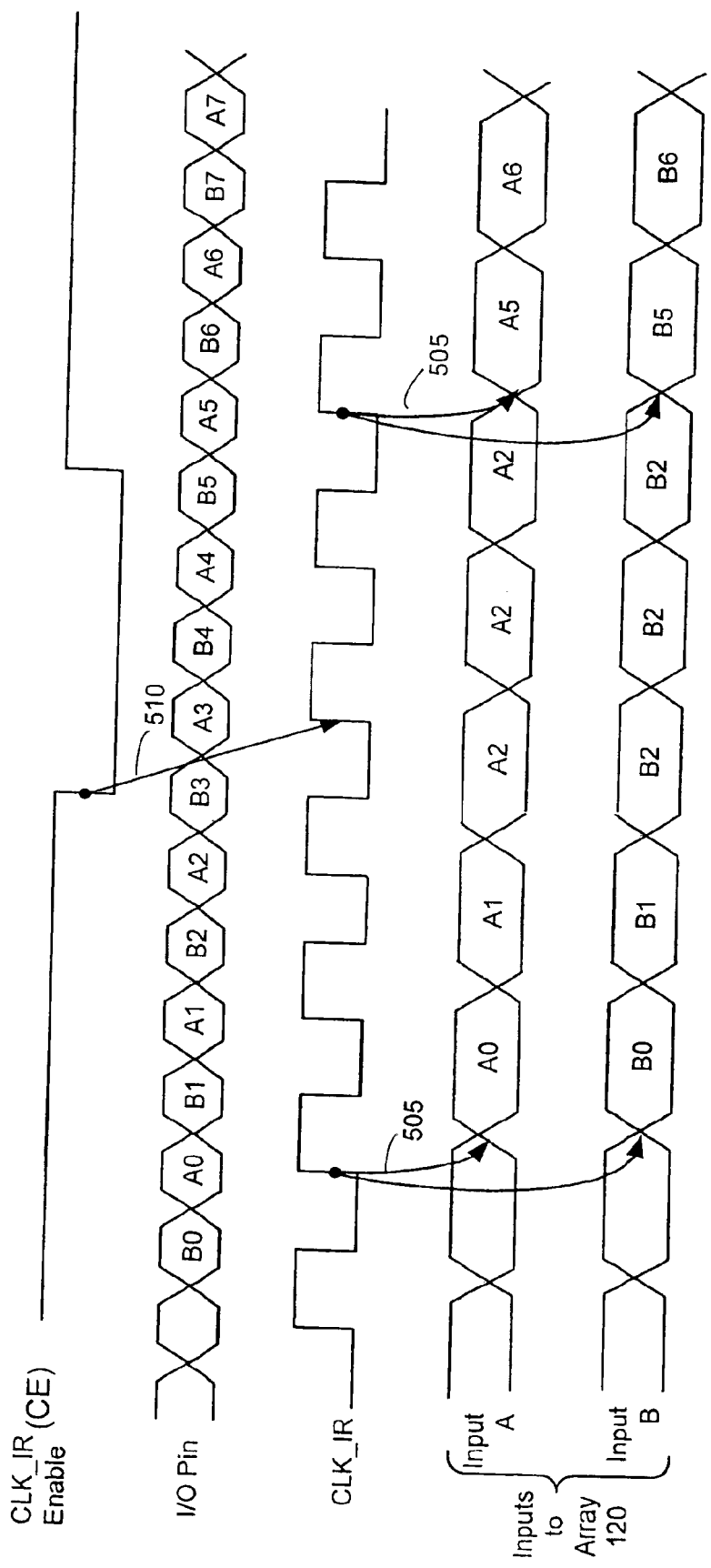
FIG. 5 is a timing diagram illustrating the operation of the I/O element input block in a double data rate I/O mode.

FIG. 5 is a timing diagram illustrating the operation of I/O element input block 200 in a DDR I/O mode. For the purposes of FIG. 5, it is assumed that programmable multiplexer 240 is configured to provide the output of input register 210 as the Input A signal and programmable multiplexer 250 is configured to provide the output of input latch 230 as the Input B signal. As illustrated in FIG. 5, the U/O Pin signal provides a sequence of bits B0, A0, B1, A1, . . .

at I/O terminal 110, where the B0, B1, . . . series of bits are center aligned with the falling edge of CLK_IR and the A0, A1, . . . series of bits are center aligned with the rising edge of CLK_IR. Thus, the B0 bit is clocked into input register 220 upon the falling edge of CLK_LR, the A0 bit is clocked into input register 210 upon the next rising edge of CLK_IR, the B1 bit is clocked into input register 220 upon the next falling edge of CLK_IR, and so on. Since input latch 230 is enabled by a high CLK_IR signal, the onset of which is effectively the rising edge of CLK_IR, the Input A signal output by register 210 and the Input B signal output by latch 230 are both effectively aligned with the rising edge of CLK_IR. This is illustrated at 505 in FIG. 5. As also shown at 510 in FIG. 5, when the CLK_IR enable signal is low, the output of register 210 and the output of latch 230 do not change until the first rising edge in CLK_IR after CLK_IR enable signal goes high again.

It will be appreciated that input latch 230 may be replaced by a rising edge triggered flip-flop, e.g., a D-type flip flop, without affecting the operation of input stage 200. Generally, however, a latch is preferable since it is simpler and requires less layout area. Furthermore, latch 230 can be removed and the Input B signal can alternatively be provided to logic array 120 (via programmable multiplexers 240 and 250) directly from the output of register 220, although in this case the Input A and Input B signals are aligned with different edges of the CLK_IR signal. However, it will be appreciated that in most applications, the two input data signals must eventually be synchronized to the same clock edge.

Figure 6:
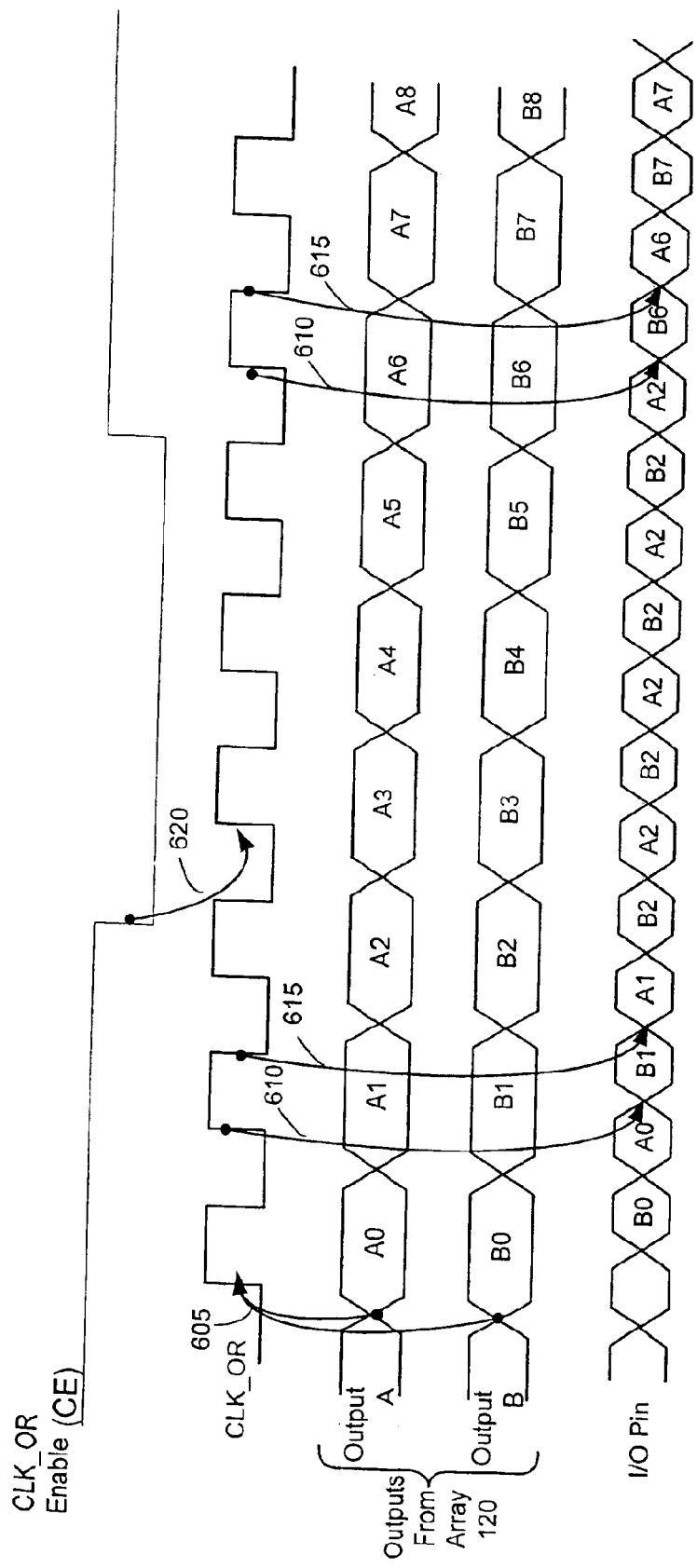
FIG. 6 is a timing diagram illustrating the operation of the I/O element output block in a double data rate I/O mode.

FIG. 6 is a timing diagram illustrating the operation of I/O element output block 300 in a DDR I/O mode. For the purposes of FIG. 6, it is assumed that programmable multiplexers 340 and 350 are configured to provide the output of multiplexer 330 (either a delayed or non-delayed version) as the signal 305 that exits output block 300. Also in DDR mode, the programmable input R in block 300 is set high.

Referring to FIG. 6, the Output A signal from array 120 provides a sequence of bits A0, A1, that are clocked into output register 310 upon the rising edge of CLK_OR. Similarly, the Output B signal from array 120 provides a sequence of bits B0, B1, that are latched by output register 320 when the latter is enabled by a high CLK_OR signal. Again, the onset of the enablement of latch 230 occurs at the rising edge of CLK_OR, so both the Output A signal and the Output B signal are effectively registered upon the rising edge of the CLK_OR signal. This is indicated at 605 in FIG. 6. Since the programmable signal R is set high, the address input to multiplexer 330 is effectively the clk signal, which as noted above has the same frequency (and preferably phase) as CLK_OR. The output of register 310 is provided as signal 305 to I/O terminal 110 when clk is low (i.e., the address input of multiplexer 330 is 0) and the output of register 320 is provided as signal 305 to I/O terminal 10 when ctk is high (i.e., the address input of multiplexer 330 is 1). Thus, with the OE OUT signal high and output driver 150 enabled, Output B bits are provided as the I/O Pin signal upon the rising edges of CLK_OR and Output A bits are provided as the I/O Pin signal upon the falling edge of CLK_OR. This is shown at 610 and 615 in FIG. 6. It will also be appreciated that output register 320 may alternatively be implemented as a rising edge triggered flip-flop, such as a D-type flip flop. In addition, as shown at 620 in FIG. 6, when the CLK_OR enable signal is low, the register output A and the latch output B do not change.

For a bidirectional DDR I/O terminal, both OE registers 410 and 420 are used. During a DDR output mode, the OE Out signal must be high (active) so that output driver 150 is enabled and signal 305 is provided to I/O terminal 110. This is achieved when logic array 120 provides a high level OE signal to output enable block 400. Where OE Out is a registered signal, i.e., multiplexer 440 is configured to select the output of OR gate 430, OE Out goes high upon the next rising edge in the CLK_OR signal. When the OE signal goes low, OE Out remains high until after both register 410 and register 420 are triggered low. In the embodiment of FIG. 4, this does not occur until the completion of the next full positive CLK_OR half cycle (i.e., at a CLK_OR falling edge) after OE becomes inactive. This is typically necessary to support bidirectional DDR memory devices such as DDR SDRAM. The bottom path of delay circuit 450 in block 400, i.e. through multiplexer 452, may be used in a DDR (or SDR) I/O mode to optionally provide a programmable delay in the OE OUT signal. The upper path of delay circuit 450, i.e., through AND gate 454, is particularly suitable for a ZBT I/O mode as described below.

The ZBT mode of operation is effectively a single data rate bidirectional mode in which there are no idle bus cycles during back-to-back read/write and back-to-back write/read cycles, thereby providing 100% bus utilization. When I/O element 100 operates in a ZBT I/O mode, input register 210, output register 310, and OE register 410 are the only bistable circuits needed in blocks 200, 300, and 400 respectively. Although the operation of I/O element 100 in a ZBT I/O mode is similar to that described above in connection with a SDR I/O mode, a serious concern in ZBT applications is the increased potential for bus contention. Bus contention occurs when two or more devices—e.g., a memory controller with logic array 120 and an associated ZBT SRAM device—are output enabled at the same time and each device attempts to drive the same bidirectional node on the bus to opposite logic values. This results in an undesirable current path between the two contending devices. Due to the lack of idle bus cycles between reads and writes in a ZBT I/O mode, the possibility of such contention occurring is heightened when a bidirectional I/O terminal of logic array 120 switches between input (read) and output (write) operations.

Figure 7:
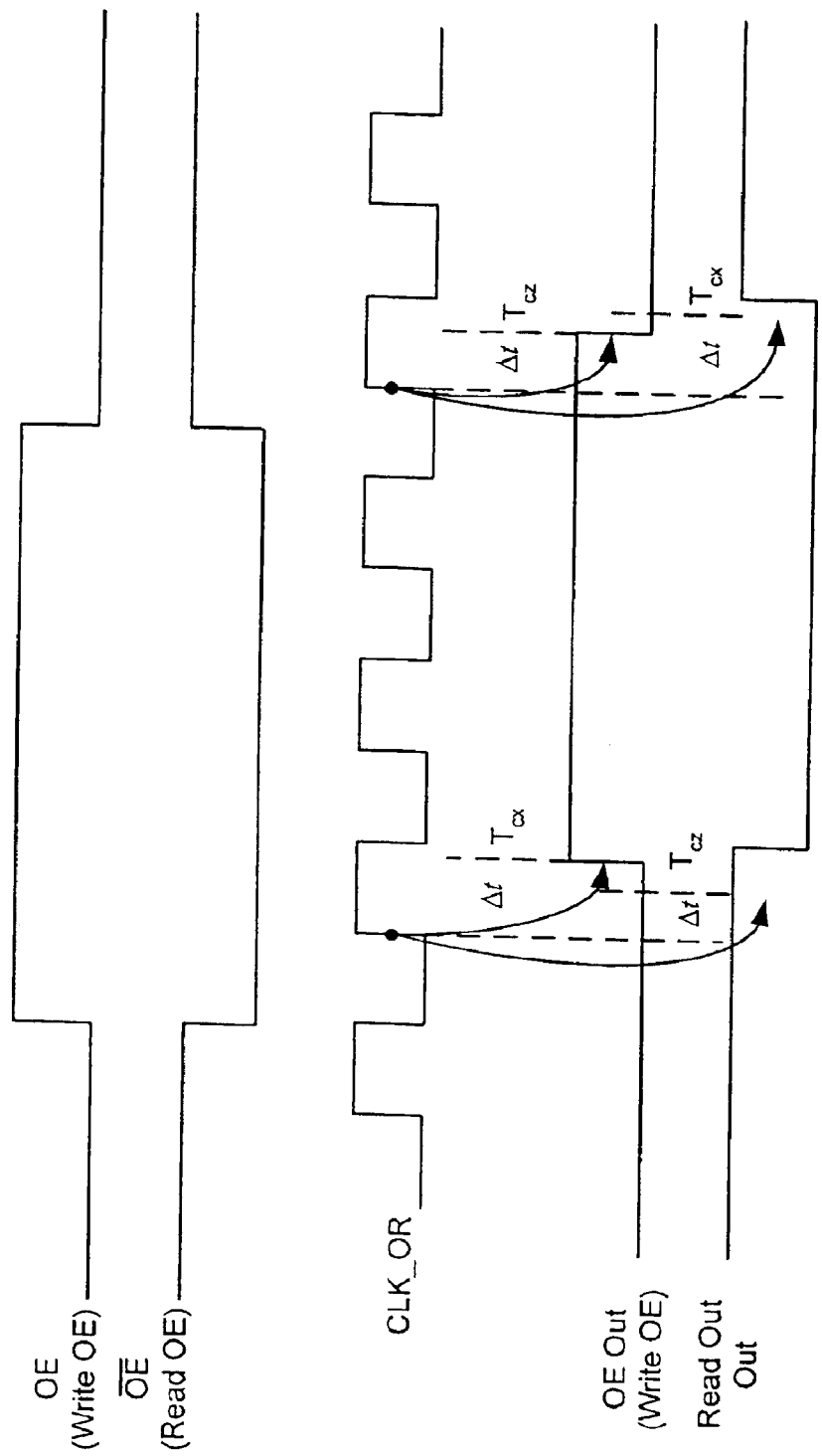
FIG. 7 is a timing diagram illustrating how bus contention is avoided in a zero bus turnaround I/O mode.

FIG. 7 is a timing diagram illustrating how bus contention can be avoided in a ZBT I/O mode by appropriately configuring delay circuit 450 in output enable block 400. FIG. 7 shows an OE signal which, as described above, is input to output enable block 400 to provide an OE OUT signal that enables output buffer (driver) 150 when high. When this occurs, an associated ZBT device can be written to. In ZBT I/O mode, OE register 420 is cleared so that the output of OR gate 430 is effectively the output of OE register 410. The complement of the OE signal (Read OE) is also shown in FIG. 7. This signal is used to generate a READ OE Out control signal that is provided to the ZBT device to control, i.e., gate, tri-state output drivers on the ZBT device when it is being read from by array 120. Although not shown, a register circuit similar to that in output enable block 400 (in particular, register 410 and delay circuit 450) may be used to generate an active high READ OE Out control signal from the complement of the OE signal (Read OE).

In the illustrated embodiment, both OE Out and READ OE Out actively enable their corresponding output buffers when high and disable those buffers when low. By configuring multiplexer 456 to provide the output of AND gate 454 as the OE Out signal, delay circuit 450 can be configured to provide a slower turn-on time (Tcx) than turn-off time (Tcz) in that signal to avoid bus contention. Similarly, the READ OE register circuit can be configured so that the READ OE Out signal is similarly provided from the output of an AND gate in a delay circuit similar to circuit 450. In this embodiment, the turn-on time Tcx is defined as the time from the triggering clock edge until the OE Out signal goes high and allows the output of buffer 150 to enter a low-impedance state. Conversely, the turn-off time Tcz is defined as the time from the triggering clock edge until the OE Out signal goes low and places the output of buffer 150 into an inactive high-impedance state. Where Tcz<Tcx for OE Out and READ OE Out as shown in FIG. 7, bus contention is avoided since neither of the interfacing devices is in an active or enabled output state at the same time.

It will be appreciated that if, on the other hand, the OE Out and READ OE Out signals are active low, i.e., they enable output buffers when in a low state, the logic circuitry in the upper path of delay circuit 450 can be suitably modified to keep Tcz<Tcx. For example, AND gate 450 can be replaced by an OR gate (not shown) so that OE Out and READ CE Out are never both low (active) at the same time in this case.

While the invention has been described in conjunction with specific embodiments, it is evident that various alternatives, modifications, and variations will be apparent to those skilled in the art. For example, in output block 300, AND gate 335 may be replaced by an OR gate which receives the clk and R signals as inputs, so that when R is 0 the address input is the clk signal and when R is 1 the address input is 1. By switching the addresses corresponding to the signals input to multiplexer 330, the same address selection functionality as that described above can be achieved. Numerous other alternatives, modifications, and variations will be apparent to those skilled in the art in light of the foregoing description.

What is claimed is:

1. A double data rate compatible input/output (I/O) element circuit for an I/O terminal of logic array comprising:

a first input register having an input for receiving a signal at the I/O terminal and an output for registering the I/O terminal signal upon a first edge in an input clock signal, the output of the first input register being connectable to the logic array, a first output register having an input for receiving a first output signal from the logic array and an output for registering the first output signal upon a first edge in an output clock signal, a second output register having an input for, in at least one mode of operation, receiving a second output signal from the logic array and an output for registering the second output signal upon a first edge in the output clock signal, a multiplexer having a first input connected to the output of the first output register, a second input connected to the output of the second output register, an address input configurable to receive the output clock signal, and an output connectable to the I/O terminal.

2. The I/O element circuit of claim 1 wherein the first output register is a delay type flip flop circuit and the second output register is a delay type latch circuit.

3. The I/O element circuit of claim 1 wherein the address input of the multiplexer in the output block circuit is configurable to receive either the output clock signal or a fixed address signal corresponding to a multiplexer input address for the registered first output signal.

4. The I/O element circuit of claim 1 wherein both programmably delayed and non-delayed versions of the signal output by the multiplexer are connectable to the I/O terminal.

5. The I/O element circuit of claim 1 further comprising a second input register having an input for receiving a signal at the I/O terminal and an output for registering the I/O terminal signal upon a first edge in an input clock signal, the output of the second input register being connectable to the logic array.

6. The I/O element circuit of claim 5 further comprising an input bistable circuit having an input for receiving the registered I/O terminal signal output by the second input register and an output for latching the registered I/O terminal signal upon the first edge in the input clock signal, the output of the bistable circuit being connectable to the logic array.

7. A first double data rate compatible input/output (I/O) element circuit for a first I/O terminal of a logic array, and a second double data rate compatible input/output (I/O) element circuit for a second I/O terminal of the logic array, wherein the first I/O element circuit comprises a first input register having an input for receiving a signal at the first I/O terminal and an output for registering the first I/O terminal signal upon a first edge in an input clock signal, the output of the first input register being connectable to the logic array, and a second input register having an input for receiving the first I/O terminal signal and an output for registering the first I/O terminal signal upon a second edge in the input clock signal, the output of the second input register being couplable to the logic array;

and the second I/O element circuit comprises a first output register having an input for receiving a first output signal from the logic array and an output for registering the first output signal upon a first edge in an output clock signal, a second output register having an input for, in at least one mode of operation, receiving a second output signal from the logic array and an output for registering the second output signal upon the first edge in the output clock signal, and a multiplexer having a first input connected to the output of the first output register, a second input connected to the output of the second output register, an address input configurable to receive the output clock signal, and an output connectable to the second I/O terminal.

8. The I/O element circuits of claim 7 wherein the first I/O element circuit further comprises an input bistable circuit having an input for receiving the registered first I/O terminal signal output by the second input register and an output for latching the registered first I/O terminal signal upon the first edge in the input clock signal, the output of the input bistable circuit being connectable to the logic array.

9. The I/O element circuits of claim 8 wherein the first input register, the second input register, and the first output register are delay type flip flop circuits, and wherein the second output register and the input bistable circuit are delay type latch circuits.

10. The I/O element circuits of claim 8 wherein the input clock signal and output clock signal are provided by different clock sources.

11. A programmable input/output (I/O) element circuit for a bidirectional I/O terminal of a logic array comprising:

a first input register having an input for receiving a signal at the I/O terminal and an output for registering the I/O terminal signal upon a first edge in an input clock signal, the output of the first input register being connectable to the logic array;

a first output register having an input for receiving an output signal from the logic array and an output for registering the output signal upon a first edge in an output clock signal, the registered output signal being connectable to the I/O terminal via a gated output buffer; and an output enable circuit for receiving an enable signal from the logic array and providing an output enable signal to a gating input of the gated output buffer.

12. The I/O element circuit of claim 11 wherein the output enable signal is provided to the gating input via a programmable delay circuit such that the gated output buffer has a slower turn-on time than turn-off time.

13. The I/O element circuit of claim 12 wherein the programmable delay circuit comprises a logic gate having first and second inputs and an output, the first logic gate input receiving a signal input to the programmable delay circuit, the second logic gate input receiving a delayed version of the signal input to the programmable delay circuit, and the output of the logic gate providing the output enable signal.

14. The I/O element circuit of claim 13 wherein the output enable signal enables the gated output buffer when high and wherein the logic gate in the programmable delay circuit comprises an AND gate.

15. The I/O element circuit of claim 13 wherein the output enable signal enables the gated output buffer when low and wherein the logic gate in the programmable delay circuit comprises an OR gate.

16. The I/O element circuit of claim 13 wherein the output enable circuit comprises an output enable register having an input for receiving the enable signal from the logic array and an output for providing a registered enable signal upon the first edge in the output clock signal, the registered enable signal being provided as the input to the programmable delay circuit.

17. The I/O element circuit of claim 11 further comprising a second output register having an input for, in at least one mode of operation, receiving a second output signal from the logic array and an output for registering the second output signal upon the first edge in the output clock signal.

18. The I/O element circuit of claim 17 further comprising a multiplexer having a first input connected to the output of the first output register, a second input connected to the output of the second output register, an address input configurable to receive the output clock signal, and an output connectable to the second I/O terminal.

19. The I/O element circuit of claim 11 further comprising a second input register having an input for receiving a signal at the I/O terminal and an output for registering the I/O terminal signal upon a first edge in an input clock signal, the output of the second input register being connectable to the logic array.

20. The I/O element circuit of claim 19 further comprising an input bistable circuit having an input for receiving the registered I/O terminal signal output by the second input register and an output for latching the registered I/O terminal signal upon the first edge in the input clock signal, the output of the bistable circuit being connectable to the logic array.

* * * * *